United States Patent
Ji et al.

(10) Patent No.: US 12,042,144 B2
(45) Date of Patent: Jul. 23, 2024

(54) RESET MECHANISM, STAPLER, AND MEDICAL DEVICE

(71) Applicant: EZISURG MEDICAL CO. LTD., Shanghai (CN)

(72) Inventors: Jiafu Ji, Shanghai (CN); Renmu Tan, Shanghai (CN); Honglin Nie, Shanghai (CN); Lei Wang, Shanghai (CN); Jun Yang, Shanghai (CN)

(73) Assignee: EZISURG MEDICAL CO. LTD., Shanghai (CN)

( * ) Notice: Subject to any disclaimer, the term of this patent is extended or adjusted under 35 U.S.C. 154(b) by 400 days.

(21) Appl. No.: 17/432,896

(22) PCT Filed: Feb. 11, 2020

(86) PCT No.: PCT/CN2020/074718
§ 371 (c)(1),
(2) Date: Aug. 20, 2021

(87) PCT Pub. No.: WO2020/168941
PCT Pub. Date: Aug. 27, 2020

(65) Prior Publication Data
US 2022/0054125 A1 Feb. 24, 2022

(30) Foreign Application Priority Data
Feb. 21, 2019 (CN) .......................... 201910135333.8

(51) Int. Cl.
*A61B 17/068* (2006.01)
*A61B 17/00* (2006.01)

(52) U.S. Cl.
CPC .. *A61B 17/068* (2013.01); *A61B 2017/00398* (2013.01); *A61B 2017/00407* (2013.01)

(58) Field of Classification Search
CPC ........ A61B 17/068; A61B 2017/00398; A61B 2017/00407; A61B 17/072
See application file for complete search history.

(56) References Cited

U.S. PATENT DOCUMENTS 8,011,551 B2 * 9/2011 Marczyk .............. A61B 17/068
227/175.1
8,056,787 B2 * 11/2011 Boudreaux ...... A61B 17/07207
227/176.1

(Continued)

FOREIGN PATENT DOCUMENTS

CN 102176869 A 9/2011
CN 105919641 A * 9/2016 ....... A61B 17/00234

(Continued)

OTHER PUBLICATIONS

International Search Report and Written Opinion mailed Apr. 26, 2020 in International Patent Application PCT/CN2020/074718.

*Primary Examiner* — Gloria R Weeks
*Assistant Examiner* — Mobeen Ahmed
(74) *Attorney, Agent, or Firm* — Venable LLP (57) ABSTRACT

The present teaching relates to a reset apparatus including a first transmission mechanism, a first rotary transmission mechanism, a one-way rotary transmission mechanism, and a second rotary transmission mechanism; a stapler; and a medical device. The one-way rotary transmission mechanism only rotates in a set direction, and is connected with the second rotary transmission mechanism, and drives the same to rotate towards the set direction. In a first state, the first transmission mechanism is connected with the first rotary transmission mechanism which drives the first transmission mechanism to act along the set direction. In a second state, the first transmission mechanism is connected with the second rotary transmission mechanism which drives the first transmission mechanism to act along the set direction. The (Continued)

present invention achieves manual resetting when the device is accidentally shut down, and is simple in structure, and safe and reliable in use.

19 Claims, 4 Drawing Sheets

(56) References Cited

U.S. PATENT DOCUMENTS

| | | | | |
|---|---|---|---|---|
| 8,608,045 B2* | 12/2013 | Smith | ............... | A61B 17/10 227/181.1 |
| 2006/0175375 A1* | 8/2006 | Shelton | ............... | A61B 17/07207 227/176.1 |
| 2008/0237298 A1* | 10/2008 | Schall | ............... | A61B 17/07207 227/180.1 |
| 2009/0090763 A1* | 4/2009 | Zemlok | ............... | A61B 17/07207 227/175.2 |
| 2010/0001036 A1* | 1/2010 | Marczyk | ............... | A61B 17/07207 227/175.1 |
| 2010/0089970 A1* | 4/2010 | Smith | ............... | G16Z 99/00 227/175.1 |
| 2011/0000025 A1* | 1/2011 | Johnson | ............... | B25B 15/008 7/168 |
| 2012/0080477 A1* | 4/2012 | Leimbach | ............... | H01M 10/42 227/175.2 |
| 2012/0241494 A1* | 9/2012 | Marczyk | ............... | A61B 17/068 227/175.1 |
| 2014/0001235 A1* | 1/2014 | Shelton, IV | ............... | A61B 17/068 227/176.1 |
| 2014/0014704 A1* | 1/2014 | Onukuri | ............... | C10M 169/00 227/175.1 |
| 2014/0239043 A1* | 8/2014 | Simms | ............... | A61B 17/07207 227/176.1 |
| 2015/0076205 A1* | 3/2015 | Zergiebel | ............... | A61B 17/07207 227/175.1 |
| 2015/0209035 A1* | 7/2015 | Zemlok | ............... | A61B 17/07207 73/1.01 |
| 2015/0297205 A1* | 10/2015 | Zergiebel | ............... | A61B 17/00 606/130 |
| 2016/0058444 A1* | 3/2016 | Shelton, IV | ............... | A61B 17/07207 227/177.1 |
| 2016/0174984 A1* | 6/2016 | Smith | ............... | A61B 17/105 227/176.1 |
| 2017/0281189 A1* | 10/2017 | Nalagatla | ............... | A61B 17/115 |
| 2017/0290583 A1* | 10/2017 | Reed | ............... | A61B 17/07207 |
| 2017/0319287 A1* | 11/2017 | Zergiebel | ............... | A61B 17/072 |
| 2018/0049835 A1* | 2/2018 | Shelton, IV | ............... | A61B 34/32 |
| 2018/0271608 A1* | 9/2018 | Ragosta | ............... | F16H 55/17 |
| 2019/0069896 A1* | 3/2019 | Satti, III | ............... | A61B 17/07207 |
| 2019/0261984 A1* | 8/2019 | Nelson | ............... | A61B 17/07207 |
| 2020/0205817 A1* | 7/2020 | Nielsen | ............... | A61B 17/1155 |
| 2020/0375674 A1* | 12/2020 | Overmyer | ............... | A61B 17/068 |
| 2020/0405306 A1* | 12/2020 | Shelton, IV | ............... | A61B 17/07207 |
| 2021/0322007 A1* | 10/2021 | Satti, III | ............... | A61B 17/068 |
| 2022/0015795 A1* | 1/2022 | Nie | ............... | A61B 17/320092 |
| 2022/0079586 A1* | 3/2022 | Shelton, IV | ............... | A61B 17/068 |
| 2022/0096066 A1* | 3/2022 | Beckman | ............... | A61B 17/00 |
| 2022/0096083 A1* | 3/2022 | Beckman | ............... | A61B 34/30 |
| 2022/0096084 A1* | 3/2022 | Beckman | ............... | A61B 34/76 |
| 2022/0133317 A1* | 5/2022 | Von Stein | ............... | A61B 17/07207 227/175.1 |
| 2022/0133318 A1* | 5/2022 | Hudson | ............... | A61B 90/98 227/175.1 |
| 2022/0202417 A1* | 6/2022 | Wenchell, Jr. | ............... | A61B 34/30 |

FOREIGN PATENT DOCUMENTS

| | | | | |
|---|---|---|---|---|
| CN | 105997171 A | * | 10/2016 | ....... A61B 17/07207 |
| CN | 206080596 U | * | 4/2017 | |
| CN | 107550531 A | * | 1/2018 | |
| CN | 105997171 A | | 8/2018 | |
| CN | 108969041 A | | 12/2018 | |
| CN | 109199488 A | | 1/2019 | |
| CN | 109730735 A | | 5/2019 | |
| WO | WO-2020228600 A1 | * | 11/2020 | ....... A61B 17/07207 |

* cited by examiner

RESET MECHANISM, STAPLER, AND MEDICAL DEVICE

CROSS REFERENCE TO RELATED APPLICATION

This application is a national stage application, filed under 35 U.S.C. § 371, of International Application PCT/CN2020/074718, filed on Feb. 11, 2020, entitled "RESET MECHANISM, ANASTOMAT, AND MEDICAL DEVICE," which claims priority to Chinese Patent Application 201910135333.8 filed on Feb. 21, 2019, which are incorporated herein by reference in their entireties.

TECHNICAL FIELD

The invention belongs to the technical field of surgical medical devices, and relates to a stapler, in particular to a reusable stapler and its reset mechanism.

BACKGROUND ART

In recent years, some medical devices, with resetting structures, have appeared on the market, such as staplers (especially electric staplers), electrosurgical instruments, and so on. The resetting structures of existing medical devices are relatively complicated and inconvenient to be operated; and the instruments may be unable to be used continuously as normal, after resetting, resulting in the instrument being scrapped.

The electric stapler is one of the above-mentioned medical device that needs reset mechanism. In case of mechanical, electronic or software failure during use of the electric stapler, the motor would stop working or fail to work normally, and then the cutting knife cannot be returned by means of driving by the motor. At this time, a fault reset mechanism is needed to allow the user to manually retract the cutting knife safely. And after clearing the trouble, the electric stapler can be restored to the initial state, so that it can be re-used continuously.

In view of this, it is urgently needed to design a new medical device in order to overcome the above-mentioned shortcomings of existing medical device.

SUMMARY

The invention provides a reset mechanism, a stapler and medical device, which can perform the mechanical resetting in the case of an unexpected shutdown of the instrument. It is of a simple structure, and is safe and reliable in use.

In order to solve the above technical problems, according to one aspect of the present invention, the following technical solutions are adopted.

A resetting device is provided. The resetting device comprises: a first transmission mechanism, a first rotation transmission mechanism, a one-way rotation transmission mechanism, and a second rotation transmission mechanism, wherein: under action of external force, the one-way rotation transmission mechanism can rotate only in one direction toward a preset direction; the one-way rotation transmission mechanism is connected with the second rotation transmission mechanism and can drive the second rotation transmission mechanism to rotate toward the preset direction; when the first rotation transmission mechanism is in a first state, the first transmission mechanism is connected to the first rotation transmission mechanism, wherein rotation of the first rotation transmission mechanism can drive the first transmission mechanism to move in a preset direction; and when the first rotation transmission mechanism is in a second state, the first transmission mechanism is connected to the second rotation transmission mechanism, and rotation of the second rotation transmission mechanism can drive the first transmission mechanism to move in a preset direction.

In one embodiment of the present invention, when the first rotation transmission mechanism is in the first state, the first transmission mechanism is connected to the first rotation transmission mechanism, and rotation of the first rotation transmission mechanism can drive the first transmission mechanism to move in a preset first direction; and when the first rotation transmission mechanism is in the second state, the first transmission mechanism is connected to the second rotation transmission mechanism, and rotation of the second rotation transmission mechanism can drive the first transmission mechanism to move in a preset second direction, and the second direction is opposite to the first direction.

In one embodiment of the present invention, the one-way rotation transmission mechanism is a ratchet, and the second rotation transmission mechanism is a second gear, wherein only when the one-way rotation transmission mechanism is rotating in the preset first direction, the second rotation transmission mechanism can be driven to rotate; and when the one-way rotation transmission mechanism is rotating in the second direction, the second rotation transmission mechanism cannot be driven to rotate.

In one embodiment of the present invention, the resetting device further comprises a switching mechanism, which is arranged close to the first rotation transmission mechanism, wherein when the switching mechanism is in a first state, the first rotation transmission mechanism is connected to the first transmission mechanism; and when the switching mechanism is in a second state, the first rotation transmission mechanism is disconnected from the first transmission mechanism.

In one embodiment of the present invention, the switching mechanism comprises a resetting cover plate, and the resetting cover plate is connected to the first rotation transmission mechanism, wherein when the resetting cover plate is in a closed state, the first transmission mechanism is connected to the first rotation transmission mechanism, and rotation of the first rotation transmission mechanism can drive the first transmission mechanism to move in a preset first direction, and the above state is a first state of the resetting cover plate; and when the resetting cover plate rotates by a set angle along a rotation axis of the resetting cover plate, the first rotation transmission mechanism is disconnected from the first transmission mechanism, and the above state is a second state of the resetting cover plate.

In one embodiment of the present invention, when the switching mechanism is in a first state, the first rotation transmission mechanism is connected to the first transmission mechanism, rotation of the first rotation transmission mechanism can drive the first transmission mechanism to move in a preset direction, and the second rotation transmission mechanism is disconnected from the first transmission mechanism; and when the switching mechanism is in a second state, the first rotation transmission mechanism is disconnected from the first transmission mechanism, the second rotation transmission mechanism is connected to the first transmission mechanism, and rotation of the second rotation transmission mechanism can drive the first transmission mechanism to move in a preset direction.

In one embodiment of the present invention, one end of the resetting cover plate is of a cam structure, and the cam structure is connected to the first rotation transmission mechanism.

In one embodiment of the present invention, the first rotation transmission mechanism is provided with a resetting elastic mechanism, wherein during process of switching the switching mechanism from the first state to the second state, the resetting elastic mechanism resets the first rotation transmission mechanism, so that the first rotation transmission mechanism is connected with the first transmission mechanism.

In one embodiment of the present invention, the first transmission mechanism is a rack, the first rotation transmission mechanism is a first gear, the one-way rotation transmission mechanism is a ratchet, and the second rotation transmission mechanism is a second gear, wherein when the first gear is in a first state, the rack is engaged with the first gear, and rotation of the first gear can drive the rack to move in a preset direction; and when the first gear is in a second state, the rack is engaged with the second gear, and rotation of the second gear can drive the rack to move in a preset direction.

In one embodiment of the present invention, the one-way rotation transmission mechanism is provided with a second operation hole, and the second operation hole can be connected with a resetting wrench, wherein when the resetting wrench is rotated toward a preset direction, the one-way rotation transmission mechanism can be driven by the resetting wrench to rotate toward the preset direction.

In one embodiment of the present invention, the resetting device further comprises a resetting wrench, which can be connected with the one-way rotation transmission mechanism, to drive the one-way rotation transmission mechanism to rotate toward a preset direction.

In one embodiment of the present invention, the resetting wrench comprises a resetting wrench base and a resetting wrench pin, and one end of the resetting wrench base is rotatably connected to one end of the resetting wrench pin.

A stapler is provided. The stapler comprises the resetting device mentioned above.

In one embodiment of the present invention, the stapler comprises a housing, the resetting device comprises a resetting cover plate, the housing is provided with a first notch, and the resetting cover plate can cover the first notch in a first state, which is a first state of a resetting cover plate; and a second state of the resetting cover plate is the state when the resetting cover plate rotates by a set angle along its rotation axis; and the resetting device also comprises a resetting wrench, the resetting wrench comprises a resetting wrench base and a resetting wrench pin, one end of the resetting wrench base is rotatably connected to one end of the resetting wrench pin; and the housing is provided with a slot for accommodating the resetting wrench.

In one embodiment of the present invention, the stapler is an electric stapler. The stapler further comprises a power mechanism, a third rotation transmission mechanism, and an actuating mechanism, wherein an output shaft of the power mechanism is connected to the third rotation transmission mechanism, and the third gear is engaged with the first rotation transmission mechanism; and the first transmission mechanism is connected to the actuating mechanism and can drive the actuating mechanism to work; and when the first rotation transmission mechanism is engaged with the first transmission mechanism, the power mechanism can drive the first transmission mechanism to work, through transmissions of the third rotation transmission mechanism and the first rotation transmission mechanism.

In one embodiment of the present invention, the stapler comprises a housing, the housing is provided with a first notch, and the housing is provided with a first operation hole, and the resetting device comprises a resetting cover plate.

A first end of the resetting cover plate is provided with a rotating shaft and a first elastic mechanism, and a second end of the resetting cover plate is provided with a slider.

When the slider is in a first position, the resetting cover plate can cover the first notch; and when the slider is in a second position, the resetting cover plate is opened to be at a certain angle, under action of the first elastic mechanism.

The slider is provided with an inclined surface, and a second elastic mechanism is provided on one side of the slider, wherein the inclined surface of the slider is located below the first operation hole.

The resetting wrench comprises a resetting wrench base and a resetting wrench pin, wherein when the resetting wrench pin is in a situation of being inserted into the first operation hole, the resetting wrench pin can push the slider to move, so that the slider moves from the first position to the second position; and in a situation that the resetting wrench pin moves away from the first operation hole, the slider is reset under driving of the second elastic mechanism located at one side.

A medical device is provided, and the medical device comprises the resetting device mentioned above.

The beneficial effects of the present invention are: the reset mechanism, the stapler and the medical device proposed by the present invention cleverly use the ratchet structure to drive the rack to reset, with the principle simple and reliable; and it will not affect the realization of the normal function of the electric stapler; the resetting cover plate can be opened only with a matching resetting wrench, which is safe and prevents misoperation; and the resetting wrench is assembled at the end of the instrument for easy installation and removal.

The entire design concept is to make operation simple, and no additional tool is required, which allows users to use it with confidence, thus solving the problem of the mechanical resetting in the event of an unexpected shutdown of the instrument. The invention provides safety protection for operations applied to a patient, and allows the user to continuously use the instrument normally after the fault resetting operation.

DETAILED DESCRIPTION OF EMBODIMENTS

The preferred embodiments of the present invention will be described in detail below with reference to the accompanying drawings.

In order to further understand the present invention, the preferred embodiments of the present invention will be described below in conjunction with examples, but it should be understood that these descriptions are only for further illustrating the features and advantages of the present invention, rather than limiting the claims of the present invention.

The description in this part is only for a few typical embodiments, and the present invention is not limited to the scope of the description of the embodiments. The same or similar existing technical means may replace some technical features in the embodiments, which is also within the scope of protection defined by the present invention.

The present invention discloses a resetting device, which can be used for the resetting of staplers (such as, electric staplers, manual staplers, and other medical devices that need to be reset, or even other instruments). The resetting device comprises: a first transmission mechanism, the first rotation transmission mechanism, the one-way rotation transmission mechanism, and the second rotation transmission mechanism. Under the action of external force, the one-way rotation transmission mechanism can rotate only in one direction toward a preset direction; the one-way rotation transmission mechanism is connected with the second rotation transmission mechanism and can drive the second rotation transmission mechanism to rotate toward the preset direction. When the first rotation transmission mechanism is in the first state, the first transmission mechanism is connected to the first rotation transmission mechanism, and the rotation of the first rotation transmission mechanism can drive the first transmission mechanism to move in a preset direction. When the first rotation transmission mechanism is in the second state, the first transmission mechanism is connected to the second rotation transmission mechanism, and the rotation of the second rotation transmission mechanism can drive the first transmission mechanism to move in the preset direction (seeing FIG. 5).

In an embodiment of the present invention, the one-way rotation transmission mechanism is a ratchet, and the second rotation transmission mechanism is a second gear; only when rotating in the preset first direction, the one-way rotation transmission mechanism can drive the second rotation transmission mechanism to rotate; and when rotating in the second direction, the one-way rotation transmission mechanism cannot drive the second rotation transmission mechanism to rotate.

Figure 5:
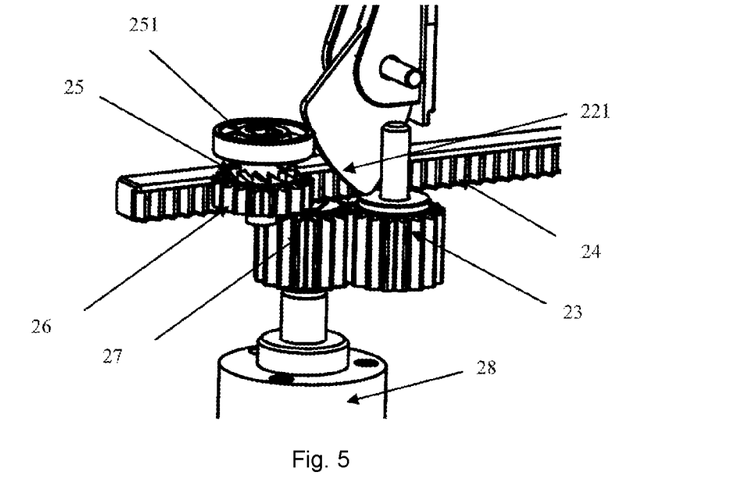
FIG. 5 is a schematic structural diagram of an embodiment of the present invention, showing that the resetting cam mechanism presses down the gear to disengage it from the rack.

FIG. 5 is a schematic structural diagram of an embodiment of the present invention showing that the resetting cam mechanism presses down the gear to make it disengaged from the rack. Referring to FIG. 5, in an embodiment of the present invention, the first transmission mechanism is a rack 24. The first rotation transmission mechanism is a first gear 23, the one-way rotation transmission mechanism is a ratchet 25, and the second rotation transmission mechanism is a second gear 26. When the first gear 23 is in the first state, the rack 24 is engaged with the first gear 23, and the rotation of the first gear 23 can drive the rack 24 to move in the preset direction. When the first gear 23 is in the second state, the rack 24 is engaged with the second gear 26, and the rotation of the second gear 26 can drive the rack 24 to move in a preset direction.

In an embodiment of the present invention, when the first rotation transmission mechanism is in the first state, the first transmission mechanism is connected to the first rotation transmission mechanism, and the rotation of the first rotation transmission mechanism can drive the first transmission mechanism to move along the preset first direction. When the first rotation transmission mechanism is in the second state, the first transmission mechanism is connected to the second rotation transmission mechanism, and the rotation of the second rotation transmission mechanism can drive the first transmission mechanism to move in the preset second direction; and the second direction is opposite to the first direction.

Referring to FIG. 5, in an embodiment of the present invention, the switching mechanism comprises a resetting cover plate 22, wherein one end of the resetting cover plate 22 is a cam structure 221, and the cam structure 221 is connected to the first rotation transmission mechanism (such as the first gear 23). When the resetting cover plate 22 is in the closed state, the first transmission mechanism (such as the rack 24) is connected to the first rotation transmission mechanism (such as the first gear 23), and the rotation of the first rotation transmission mechanism (such as the first gear 23) can drive the first transmission mechanism (such as the rack 24) to move in the preset first direction, and the above state is the first state of the resetting cover plate 22. When the resetting cover plate 22 rotates by a set angle along its rotation axis 222, the first rotation transmission mechanism (such as the first gear 23) is disconnected from the first transmission mechanism (such as the rack 24), and the above state is the second state of the resetting cover plate 22.

Figure 6:
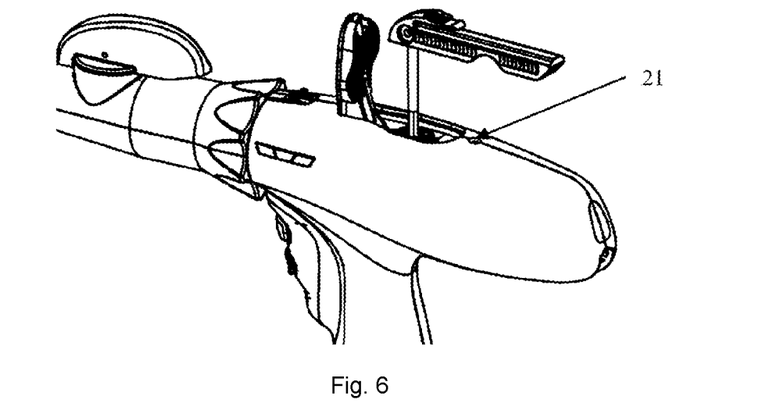
FIG. 6 is a schematic structural diagram of an embodiment of the present invention showing that the resetting wrench is in the ratchet operation hole.

FIG. 6 is a schematic structural diagram of an embodiment of the present invention showing that the resetting wrench is in the ratchet operation hole. Referring to FIG. 6, in an embodiment of the present invention, the resetting device further comprises a resetting wrench 1. The resetting wrench 1 can be connected with the one-way rotation transmission mechanism (such as the ratchet 25) to drive the one-way rotation transmission mechanism (such as the ratchet 25) to rotate in a preset direction.

Figure 3:
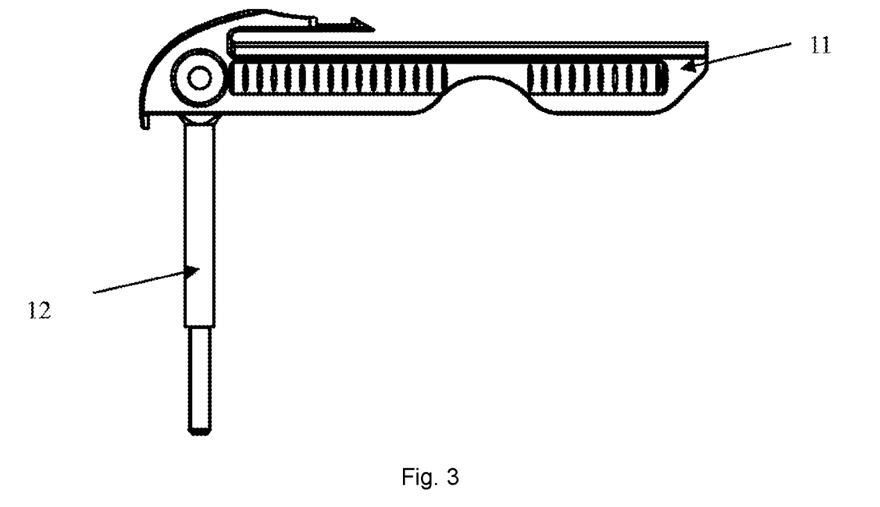
FIG. 3 is a schematic structural diagram of the resetting wrench being deployed, in an embodiment of the present invention.

FIG. 3 is a schematic structural diagram of the resetting wrench being deployed in an embodiment of the present invention. Referring to FIG. 3, in an embodiment of the present invention, the resetting wrench 1 comprises a resetting wrench base 11 and a resetting wrench pin 12, and the resetting wrench base 11 has one end which is rotatably connected to one end of the resetting wrench pin 12. When the resetting wrench base 11 is deployed with respect to the resetting wrench pin 12 (the two forming approximately 90° therebetween), they can be used as a wrench for easy rotation, thereby driving the ratchet to rotate. When the resetting wrench base 11 and the resetting wrench pin 12 are closed (the two are arranged approximately in parallel), it is convenient to put it into the special slot of the electric handle 2.

Figure 7:
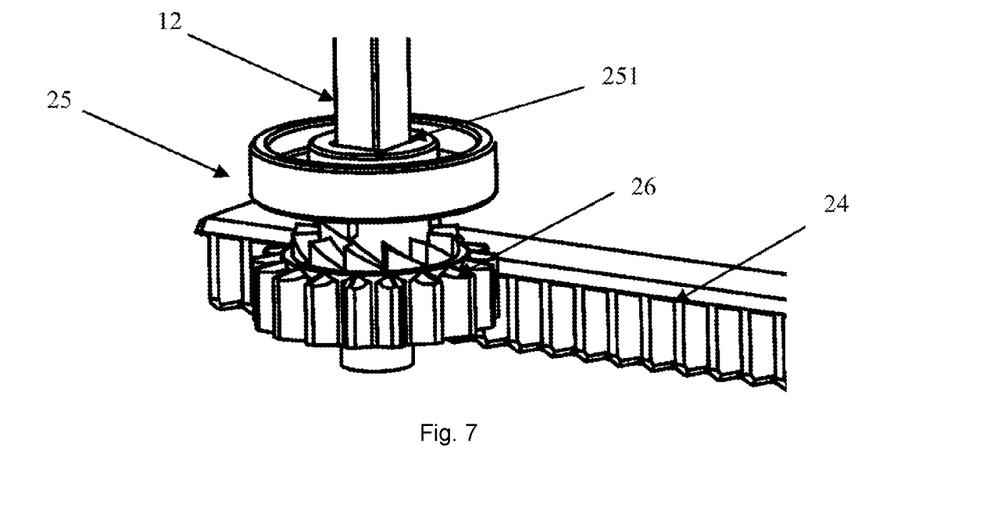
FIG. 7 is a schematic diagram of an embodiment of the present invention, showing that the resetting ratchet drives the rack to work.

FIG. 7 is a schematic diagram of an embodiment of the present invention showing that the resetting ratchet drives the rack to work. Referring to FIG. 7, in an embodiment of the present invention, the one-way rotation transmission mechanism (for example, it may be the ratchet 25) is provided with a second operation hole 251. The second operation hole 251 can be connected with a resetting wrench 1, and the resetting wrench pin of the resetting wrench 1 is inserted into the second operation hole 251. When the resetting wrench 1 rotates toward the preset direction, the ratchet 25 can be driven by the resetting wrench 1 to rotate toward the preset direction, so that the rack 24 is driven by the second gear 26 to reset.

In an embodiment of the present invention, the resetting device further comprises a switching mechanism (such as the resetting cover plate 22), and the switching mechanism is arranged close to the first rotation transmission mechanism (such as the first gear 23). When the switching mechanism is in the first state, the first rotation transmission mechanism (such as the first gear 23) is connected with the first transmission mechanism (such as the rack 24); and when the switching mechanism is in the second state, the first rotation transmission mechanism (such as the first gear 23) is disconnected from the first transmission mechanism (such as the rack 24).

In an embodiment of the present invention, when the switching mechanism is in the first state, the first rotation transmission mechanism (such as the first gear 23) is connected to the first transmission mechanism (such as the rack 24), and the rotation of the first rotation transmission mechanism (such as the first gear 23) can drive the first transmission mechanism (such as the rack 24) to move in a preset direction, and the second rotation transmission mechanism (such as the second gear 26) is disconnected from the first transmission mechanism (such as the rack 24). When the switching mechanism is in the second state, the first rotation transmission mechanism (such as the first gear 23) is disconnected from the first transmission mechanism (such as the rack 24), and the second rotation transmission mechanism (such as the second gear 26) is connected to the first transmission mechanism (such as the rack 24). The rotation of the second rotation transmission mechanism (such as the second gear 26) can drive the first transmission mechanism (such as the rack 24) to move in a preset direction.

Figure 9:
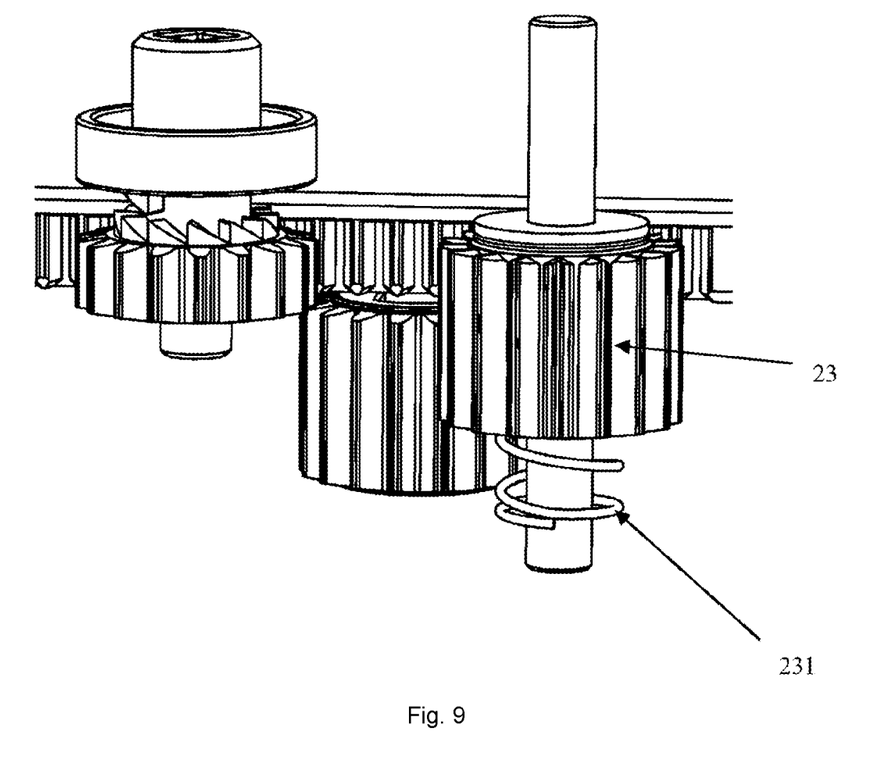
FIG. 9 is a schematic diagram of an embodiment of the present invention showing the cooperation between various transmission mechanisms in the resetting device.

FIG. 9 is a schematic diagram of an embodiment of the present invention showing the cooperation between various transmission mechanisms in the resetting device. Referring to FIG. 9, in an embodiment of the present invention, the first rotation transmission mechanism (such as the first gear 23) is provided with a resetting elastic mechanism 231. During the switching mechanism (such as the resetting cover plate 22) being switched from the first state to the second state, the resetting elastic mechanism 231 resets the first rotation transmission mechanism (such as the first gear 23), so that the first rotation transmission mechanism (such as the first gear 23) is connected with the first transmission mechanism (such as the rack 24). In an embodiment of the present invention, the resetting elastic mechanism 231 is a spring.

As shown in FIG. 9, in an embodiment of the present invention, a resetting elastic mechanism 231 is provided under the first gear 23. When the resetting cover plate 22 returns to the first state again, the first gear 23 automatically operates upward under the pushing of the resetting elastic mechanism 231. The first gear 23 is engaged with the rack 24.

The present invention also discloses an electric stapler, which comprises the above-mentioned resetting device.

In an embodiment of the present invention, the electric stapler comprises a housing, and the housing is provided with a first notch. The resetting cover plate can cover the first notch in the first state, and the state is the first state of the resetting cover plate. The second state of the resetting cover plate is the state in which it rotates by a preset angle (such as 90°) along its rotation axis. The resetting device also comprises a resetting wrench, and the resetting wrench comprises a resetting wrench base and a resetting wrench pin. One end of the resetting wrench base is rotatably connected to one end of the resetting wrench pin. The housing is provided with a slot for accommodating the resetting wrench.

Figure 1:
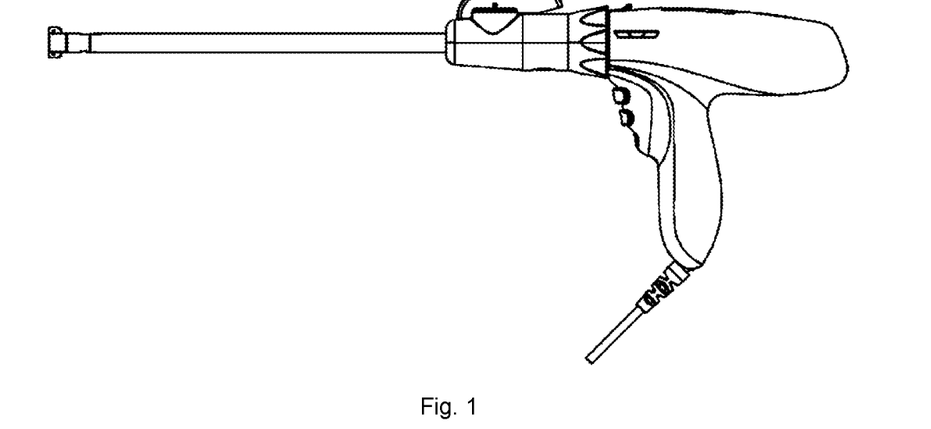
FIG. 1 is a schematic structural diagram of the electric stapler in an embodiment of the present invention.
Figure 2:
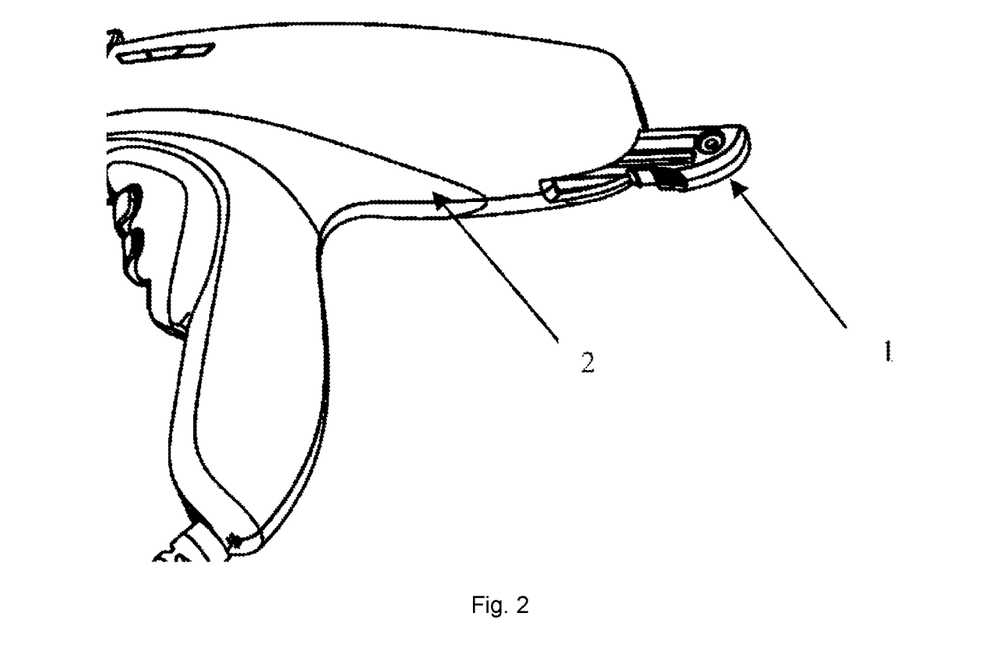
FIG. 2 is a schematic structural diagram of the electric stapler in an embodiment of the present invention with the resetting wrench taken out.

FIG. 1 is a schematic structural diagram of an electric stapler in an embodiment of the present invention, and FIG. 2 is a schematic structural diagram of an electric stapler of an embodiment of the present invention with the resetting wrench being taken out. Referring to FIG. 1 and FIG. 2 (in combination with FIG. 4), in an embodiment of the invention, the electric stapler comprises: a resetting wrench 1 and an electric handle 2, and the resetting wrench 1 is detachably mounted on the electric handle 2.

The resetting wrench 1 comprises a resetting wrench base 11 and a resetting wrench pin 12. The electric handle 2 comprises a first operation hole 21, a resetting cover plate 22, a first gear 23, a rack 24, a ratchet 25 (resetting ratchet) and a second gear 26 (resetting gear).

The resetting wrench pin 12 is provided with an end head that can be inserted into the first operation hole 21. In the situation that the resetting wrench pin 12 is inserted into the first operation hole 21, the resetting cover plate 22 is opened. The first end of the resetting cover plate 22 is provided with a cam surface 221, and the first end of the resetting cover plate 22 is located close to the gear 23. When the resetting cover plate 22 is in the first state, the first gear 23 is engaged with the rack 24. During the process that the resetting cover plate 22 is rotating from the first state to the second state, the cam surface of the resetting cover plate 22 rotates to press down the first gear 23 engaged with the rack 24, so that the first gear 23 is disengaged from the rack 24.

The ratchet 25 is provided with a second operation hole 251 (second operation hole), and the end head of the resetting wrench pin 12 can be inserted into the second operation hole 251. In the situation that the resetting wrench pin 12 is inserted into the second operation hole 251, the rotation of the resetting wrench 1 can drive the ratchet 25 to rotate.

The ratchet 25 is engaged with the second gear 26, and the rotation of the ratchet 25 can drive the second gear 26 to rotate. The second gear 26 is engaged with the rack 24, and the rotation of the second gear 26 can drive the rack 24 to move in the preset direction.

An elastic mechanism is provided under the first gear 23. The resetting cover plate 22 returns to the first state again, and the first gear 23 automatically operates upward under the pushing of the elastic mechanism, so as to be engaged with the rack 24.

In an embodiment of the present invention, referring to FIG. 5, the electric stapler further comprises a power mechanism 28, a third gear 27, and an actuating mechanism. The output shaft of the power mechanism 28 is connected to the third gear 27, and the third gear 27 is engaged with the first gear 23. The rack 24 is connected to the actuating mechanism and can drive the actuating mechanism to work (the actuating mechanism may be an actuating component such as a cutting knife). When the first gear 23 is engaged with the rack 24, the power mechanism 28 can drive the rack 24 to work by means of the transmission of the third gear 27 and the first gear 23 (the power mechanism 28 drives the third gear 27 to rotate, and the third gear 27 drives the first gear 23 to rotate).

Figure 4:
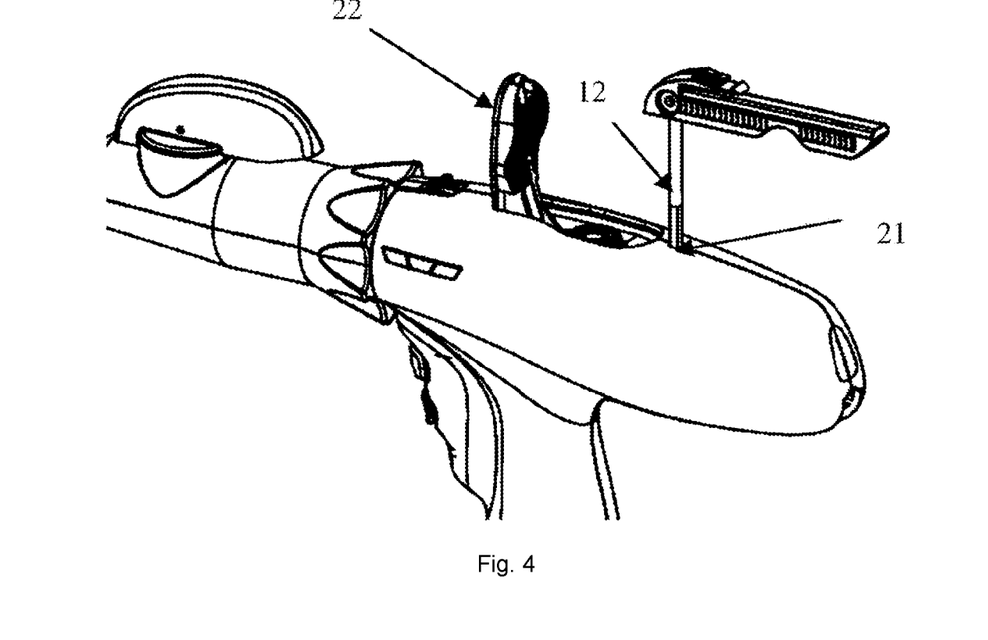
FIG. 4 is a schematic structural diagram of the resetting cover plate being opened, in an embodiment of the present invention.
Figure 8:
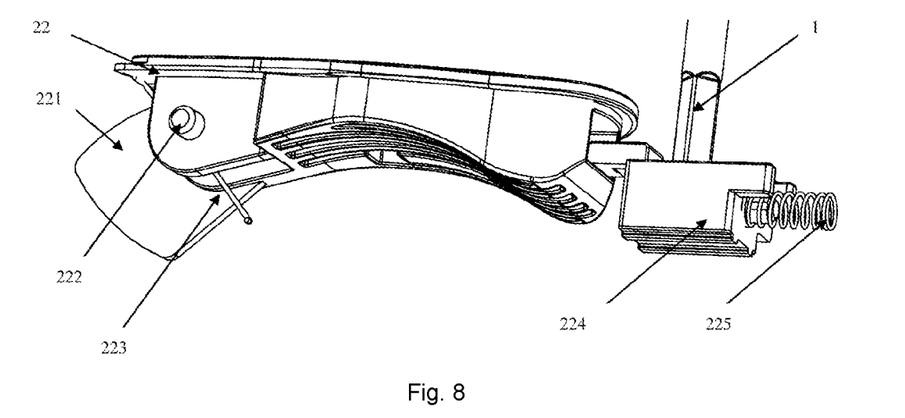
FIG. 8 is a schematic structural diagram of a resetting cover plate in an embodiment of the present invention.

FIG. 4 is a schematic structural diagram of the resetting cover plate being open, in an embodiment of the present invention. FIG. 8 is a schematic structural diagram of the resetting cover plate in an embodiment of the present invention. Referring to FIGS. 4 and 8, in an embodiment of the present invention, the stapler comprises a housing. The housing is provided with a first notch, and the housing is provided with a first operation hole 21. The resetting device comprises a resetting cover plate 22, and the first end of the resetting cover plate 22 is provided with a cam structure 221. The cam structure 221 is connected to the first gear 23. The first end of the resetting cover plate 22 is provided with a rotating shaft 222 and a first elastic mechanism 223. The second end of the resetting cover plate is provided with a slider 224.

When the slider 224 is in the first position, the resetting cover plate 22 can cover the first notch; and when the slider 224 is in the second position, the resetting cover plate 22, under action of the first elastic mechanism 223, is opened to a certain angle (in an embodiment of the present invention, the first elastic mechanism 223 may be a torsion spring). Afterwards, it can be manually moved to another angle, to move the resetting cover plate 22 to the second position. The slider 224 is provided with an inclined surface, and a second elastic mechanism 225 is provided at one side of the slider. The inclined surface of the slider 224 is located below the first operation hole.

The resetting wrench 1 comprises a resetting wrench base 11 and a resetting wrench pin 12. In the situation that the resetting wrench pin 12 is inserted into the first operation hole, the resetting wrench pin 12 can push the slider 224 to move, so that the slider 224 moves from the first position toward the second position; and in the situation that the resetting wrench pin 12 moves away from the first operation hole, the slider 224 is reset under the driving of the second elastic mechanism 225 located on one side. In an embodiment of the present invention, the second elastic mechanism 225 is a spring.

The resetting wrench 1 acts on the inclined surface of the slider (not shown in the figure), to make the slider move back, thereby releasing the resetting cover plate 22, and the resetting cover plate 22 is opened under the action of the torsion spring.

The use method of the electric stapler of the present invention is as follows.

During operation, firstly the resetting wrench 1 is taken out from the below of the electric handle 2, and the resetting wrench 1 is operated in such a way that the resetting wrench base 11 and the resetting wrench pin 12 are deployed to have a right angle therebetween, as shown in FIG. 3. Then the resetting wrench pin 12 of the resetting wrench base 11 is inserted into the resetting operation hole 21, and then the resetting cover plate 22 is opened, as shown in FIG. 4. Then, the resetting cover plate 22 is pulled and the resetting cover plate 22 is rotated to a vertical position. As shown in FIG. 4, the internal mechanism of the resetting cover plate 22 has a cam surface. During the rotation, the cam surface presses down the first gear 23 that was originally engaged with the driving rack 24, to make it disengaged from the rack 24, as shown in FIG. 5. Finally, the resetting wrench 1 is inserted into the second operation hole 251 of the resetting ratchet 25, the resetting wrench 1 reciprocally rotates, and the rack 24 is driven to move proximally through the ratchet 25 and the second gear 26, and the cutting knife is safely retracted, as shown in FIG. 6. The ratchet 25 is always in contact with the resetting gear 26 under the pressing of the internal spring. When the resetting wrench 1 is reciprocally rotated, the rack 24 can only make the cutting knife move back one-way to the proximal end, with the moving forward impossible.

After the cutting knife is retracted, the resetting cover plate 22 is closed again to return to the initial position, and the first gear 23 will be automatically engaged with the rack 24 upward. Then, the resetting wrench 1 is closed and is inserted again into the electric handle 2. The functions of the electric stapler are checked, wherein if all functions are normal, it can be continuously used.

The present invention also discloses a medical device (even other devices that need to be reset), the medical device comprising the above-mentioned resetting device.

In summary, the reset mechanism, stapler and medical device proposed by the present invention cleverly use the ratchet structure to drive the rack to reset, the principle of which is simple and reliable. It will not affect realization of the normal functions of the electric stapler. The resetting cover plate can be opened using a matching resetting wrench only, which is safe and prevents misoperation. The resetting wrench is assembled at the tail portion of the instrument, for easy installation and removal.

The entire design concept is to make the operation simple, requiring no additional tools, which allows users to use it with confidence, thus solving the problem of the mechanical resetting in the event of an unexpected shutdown of the instrument. The invention provides safety protection for operations applied to a patient, and allows the user to continuously use the instrument normally after the resetting operation if the fault occurs.

The description and use of the present invention here are illustrative, and not intended to make the scope of the present invention limited to the above-mentioned embodiments. Modifications and changes of the embodiments disclosed herein are possible, and replacements and equivalent components of the embodiments are well known to those of ordinary skill in the art. It should be clear to those skilled in the art that, without departing from the spirit or essential features of the present invention, the present invention can be implemented in other forms, structures, arrangements, proportions, or using other components, materials, and parts. Without departing from the scope and spirit of the present invention, other modifications and changes may be made to the embodiments disclosed herein.

What is claimed is:

1. A resetting device for a stapler, the resetting device comprising:
    a first transmission mechanism,
    a first rotation transmission mechanism,
    a one-way rotation transmission mechanism, and
    a second rotation transmission mechanism, wherein
    under action of external force, the one-way rotation transmission mechanism is configured to rotate only in one direction toward a first preset direction; and the one-way rotation transmission mechanism is connected with the second rotation transmission mechanism and is configured to drive the second rotation transmission mechanism to rotate toward the first preset direction;
    when the first rotation transmission mechanism is in a first state, the first transmission mechanism is connected to the first rotation transmission mechanism, wherein rotation of the first rotation transmission mechanism drives the first transmission mechanism to move in the first preset direction;

when the first rotation transmission mechanism is in a second state, the first transmission mechanism is connected to the second rotation transmission mechanism, and rotation of the second rotation transmission mechanism drives the first transmission mechanism to move in a second preset direction;

the one-way rotation transmission mechanism is provided with an operation hole, and the operation hole is configured to be connected with a resetting wrench; and the stapler comprises a housing, the housing is provided with a first notch, and the housing is provided with another operation hole, and the resetting device comprises a resetting cover plate, wherein a first end of the resetting cover plate is provided with a first elastic mechanism, and a slider is provided at one side of the resetting cover plate, when the slider is in a first position, the resetting cover plate is configured to cover the first notch; and when the slider is in a second position, the resetting cover plate is opened to be at a certain angle, under action of the first elastic mechanism;

a second elastic mechanism is provided at one side of the slider; and the resetting wrench comprises a resetting wrench base and a resetting wrench pin, wherein when the resetting wrench pin is in a situation of being inserted into the another operation hole, the resetting wrench pin is configured to push the slider to move, so that the slider moves from the first position to the second position; and in a situation that the resetting wrench pin moves away from the another operation hole, the slider is reset under driving of the second elastic mechanism located at the one side of the slider.

2. The resetting device according to claim 1, wherein: the second preset direction is opposite to the first preset direction.

3. A stapler comprising the resetting device according to claim 2.

4. A medical device comprising the resetting device according to claim 2.

5. The resetting device according to claim 1, wherein: the one-way rotation transmission mechanism is a ratchet, wherein only when the one-way rotation transmission mechanism rotates in the first preset direction, the second rotation transmission mechanism is configured to be driven to rotate; and when the one-way rotation transmission mechanism rotates in the second preset direction, the second rotation transmission mechanism cannot be driven to rotate.

6. A stapler comprising the resetting device according to claim 5.

7. The resetting device according to claim 1, wherein: the resetting device further comprises a switching mechanism, which is arranged close to the first rotation transmission mechanism, wherein when the switching mechanism is in a first state, the first rotation transmission mechanism is connected to the first transmission mechanism; and when the switching mechanism is in a second state, the first rotation transmission mechanism is disconnected from the first transmission mechanism.

8. The resetting device according to claim 7, wherein: the switching mechanism comprises a resetting cover plate, and the resetting cover plate is connected to the first rotation transmission mechanism, when the resetting cover plate is in a closed state, the first transmission mechanism is connected to the first rotation transmission mechanism, and rotation of the first rotation transmission mechanism drives the first transmission mechanism to move in the first preset direction, and the state is a first state of the resetting cover plate; and when the resetting cover plate rotates by a set angle along a rotation axis of the resetting cover plate, the first rotation transmission mechanism is disconnected from the first transmission mechanism, and the state is a second state of the resetting cover plate.

9. The resetting device according to claim 7, wherein: when the switching mechanism is in the first state, the first rotation transmission mechanism is connected to the first transmission mechanism, rotation of the first rotation transmission mechanism drives the first transmission mechanism to move in the first preset direction, and the second rotation transmission mechanism is disconnected from the first transmission mechanism; and when the switching mechanism is in the second state, the first rotation transmission mechanism is disconnected from the first transmission mechanism, the second rotation transmission mechanism is connected to the first transmission mechanism, and rotation of the second rotation transmission mechanism drives the first transmission mechanism to move in the second preset direction.

10. The resetting device according to claim 7, wherein: one end of the resetting cover plate is a cam structure, and the cam structure is connected to the first rotation transmission mechanism.

11. The resetting device according to claim 7, wherein: the first rotation transmission mechanism is provided with a resetting elastic mechanism, wherein during process of switching the switching mechanism from the first state to the second state, the resetting elastic mechanism resets the first rotation transmission mechanism, so that the first rotation transmission mechanism is connected with the first transmission mechanism.

12. The resetting device according to claim 1, wherein: the first transmission mechanism is a rack, the first rotation transmission mechanism is a first gear, the one-way rotation transmission mechanism is a ratchet, and the second rotation transmission mechanism is a second gear, wherein when the first gear is in the first state, the rack is engaged with the first gear, and rotation of the first gear drives the rack to move in the first preset direction; and when the first gear is in the second state, the rack is engaged with the second gear, and rotation of the second gear drives the rack to move in the second preset direction.

13. The resetting device according to claim 1, wherein when the resetting wrench is rotated toward the first preset direction, the one-way rotation transmission mechanism is configured to be driven by the resetting wrench to rotate toward the first preset direction.

14. The resetting device according to claim 1, wherein: the resetting wrench is configured to be connected with the one-way rotation transmission mechanism, to drive the one-way rotation transmission mechanism to rotate toward the first preset direction.

15. The resetting device according to claim 14, wherein: one end of the resetting wrench base is rotatably connected to one end of the resetting wrench pin.

16. A stapler comprising the resetting device according to claim 1.

17. The stapler according to claim 16, wherein:
the resetting cover plate is configured to cover the first notch in a first state, which is a first state of the resetting cover plate; and a second state of the resetting cover plate is the state when the resetting cover plate rotates by a set angle along its rotation axis; and
the resetting device further comprises the resetting wrench, the resetting wrench comprises the resetting wrench base and the resetting wrench pin, one end of the resetting wrench base is rotatably connected to one end of the resetting wrench pin; and the housing is provided with a slot for accommodating the resetting wrench.

18. The stapler according to claim 16, wherein:
the stapler is an electric stapler, and the stapler further comprises a power mechanism, a third gear, and an actuating mechanism, wherein an output shaft of the power mechanism is connected to the third rotation transmission mechanism, and the third gear is engaged with the first rotation transmission mechanism; and the first transmission mechanism is connected to the actuating mechanism and is configured to drive the actuating mechanism to work; and
when the first rotation transmission mechanism is engaged with the first transmission mechanism, the power mechanism is configured to drive the first transmission mechanism to work, through transmissions of the third rotation transmission mechanism and the first rotation transmission mechanism.

19. A medical device comprising the resetting device according to claim 1.

\* \* \* \* \*